United States Patent
Wang

(10) Patent No.: US 10,023,533 B2
(45) Date of Patent: Jul. 17, 2018

(54) PROCESS TO PRODUCE PARAFFINIC HYDROCARBON FLUIDS FROM LIGHT PARAFFINS

(71) Applicant: ExxonMobil Research and Engineering Company, Annandale, NJ (US)

(72) Inventor: Kun Wang, Bridgewater, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 92 days.

(21) Appl. No.: 15/387,996

(22) Filed: Dec. 22, 2016

(65) Prior Publication Data

US 2017/0101355 A1 Apr. 13, 2017

Related U.S. Application Data

(63) Continuation-in-part of application No. 14/956,477, filed on Dec. 2, 2015, now Pat. No. 9,688,626.

(60) Provisional application No. 62/092,485, filed on Dec. 16, 2014.

(51) Int. Cl.
| | |
|---|---|
| *C07C 2/76* | (2006.01) |
| *C07C 2/82* | (2006.01) |
| *C07C 29/00* | (2006.01) |
| *C10G 53/14* | (2006.01) |
| *C07C 407/00* | (2006.01) |
| *C07C 29/132* | (2006.01) |
| *C07C 29/50* | (2006.01) |
| *C10G 45/02* | (2006.01) |
| *C10G 50/02* | (2006.01) |
| *C10G 69/12* | (2006.01) |
| *C07C 2/86* | (2006.01) |

(52) U.S. Cl.
CPC ............ *C07C 407/00* (2013.01); *C07C 2/862* (2013.01); *C07C 29/132* (2013.01); *C07C 29/50* (2013.01); *C10G 45/02* (2013.01); *C10G 50/02* (2013.01); *C10G 69/126* (2013.01); *C10G 2300/1025* (2013.01); *C10G 2300/1081* (2013.01); *C10G 2400/02* (2013.01); *C10G 2400/04* (2013.01); *C10G 2400/08* (2013.01); *C10L 2290/543* (2013.01)

(58) Field of Classification Search
CPC .. C07C 2/76; C07C 2/82; C07C 29/00; C10G 53/14
USPC ................................ 585/700, 709; 568/909.8
See application file for complete search history.

(56) References Cited

U.S. PATENT DOCUMENTS

| | | | |
|---|---|---|---|
| 2,845,461 A | 7/1958 | Winkler et al. | |
| 3,478,108 A | 11/1969 | Grane | |
| 3,594,320 A | 7/1971 | Orkin | |
| 3,775,325 A | 11/1973 | Kerfoot et al. | |
| 3,862,024 A | 1/1975 | Favis | |
| 4,140,619 A | 2/1979 | van der Wiel et al. | |
| 4,175,278 A | 11/1979 | Sato et al. | |
| 4,408,081 A | 10/1983 | Foster | |
| 4,594,172 A | 6/1986 | Sie | |
| 4,618,737 A | 10/1986 | Chester et al. | |
| 4,883,581 A | 11/1989 | Dickakian | |
| 4,911,821 A | 3/1990 | Katzer et al. | |
| 4,913,794 A | 4/1990 | Le et al. | |
| 4,919,788 A | 4/1990 | Chen et al. | |
| 4,975,177 A | 12/1990 | Garwood et al. | |
| 4,990,713 A * | 2/1991 | Le .......................... | C10G 50/02 585/332 |
| 4,997,543 A | 3/1991 | Harandi et al. | |
| 5,008,460 A | 4/1991 | Garwood et al. | |
| 5,021,142 A | 6/1991 | Bortz et al. | |
| 5,037,528 A | 8/1991 | Garwood et al. | |
| 5,149,885 A | 9/1992 | Jubin, Jr. | |
| 5,162,593 A | 11/1992 | Maffia et al. | |
| 5,171,916 A | 12/1992 | Le et al. | |
| 5,243,084 A | 9/1993 | Cochran et al. | |
| 5,271,825 A | 12/1993 | Bortz et al. | |
| 5,288,919 A | 2/1994 | Faraj | |
| 5,306,416 A | 4/1994 | Le et al. | |
| 5,345,009 A | 9/1994 | Sanderson et al. | |
| 5,705,724 A | 1/1998 | Collins et al. | |
| 5,750,480 A | 5/1998 | Xiong et al. | |
| 7,034,189 B1 | 4/2006 | Kollar | |
| 7,723,556 B2 | 5/2010 | Elomari et al. | |

(Continued)

FOREIGN PATENT DOCUMENTS

| | | |
|---|---|---|
| CA | 1103913 A | 6/1981 |
| CA | 2098995 A1 | 7/1992 |

(Continued)

OTHER PUBLICATIONS

PCT/US2015/063394 International Search Report and Written Opinion dated Mar. 18, 2016.
Wallner et al., "Analytical Assessment of C2-C8 Alcohols as Spark-Ignition Engine Fuels", Proceedings of the FISITA 2012 World Automotive Congress, Nov. 7, 2012, pp. 15-26, vol. 3, Springer.
Unknown, "Advanced Motor Fuels", Implementing Agreement for Advanced Motor Fuels, http://www.iea-amf.org/content/fuel_information/butanol/properties.
Ghosh et al., "Development of a Detailed Gasoline Composition-Based Octane Model", Industrial & Engineering Chemistry Research, Nov. 24, 2005, pp. 337-345, vol. 45, iss. 1, ACS Publications.

(Continued)

*Primary Examiner* — Thuan D Dang
(74) *Attorney, Agent, or Firm* — Robert A. Migliorini

(57) ABSTRACT

A process for converting light paraffins to heavier paraffinic hydrocarbon fluids is disclosed. The process involves: (1) oxidation of iso-paraffins to alkyl hydroperoxides and alcohols; (2) conversion of the alkyl hydroperoxides and alcohols to dialkyl peroxides; and (3) radical-initiated coupling of paraffins and/or iso-paraffins using the dialkyl peroxides as radical initiators, thereby forming heavier hydrocarbon products. Fractionation of the heavy hydrocarbon products can then be used to isolate fractions for use as hydrocarbon fluids.

24 Claims, No Drawings

(56) References Cited

U.S. PATENT DOCUMENTS

| | | | |
|---|---|---|---|
| 7,732,654 | B2 | 6/2010 | Elomari et al. |
| 7,973,204 | B2 | 7/2011 | Elomari et al. |
| 2008/0253936 | A1 | 10/2008 | Abhari |
| 2016/0168048 | A1 | 6/2016 | Wang et al. |

FOREIGN PATENT DOCUMENTS

| | | | |
|---|---|---|---|
| DE | 2453863 | A1 | 5/1975 |
| DE | 298521 | A5 | 2/1992 |
| EP | 0104729 | A2 | 4/1984 |
| FR | 2210656 | A1 | 7/1974 |
| FR | 2210657 | A1 | 7/1974 |
| JP | 49034903 | A | 3/1974 |
| JP | 51012802 | A | 1/1976 |
| JP | 60108495 | A | 6/1985 |
| NL | 7510598 | A | 3/1977 |
| PL | 63556 | Y1 | 12/1969 |
| RU | 1778148 | A1 | 11/1992 |
| RU | 1810378 | A1 | 4/1993 |
| SU | 1068467 | A1 | 1/1984 |
| SU | 438293 | A1 | 11/1984 |
| SU | 1525196 | A1 | 11/1989 |
| SU | 1799902 | A1 | 3/1993 |

OTHER PUBLICATIONS

Perdih et al., "Topological Indices Derived from Parts of a Universal Matrix", Acta Chimica Slovenica, Apr. 28, 2006, pp. 180-190, vol. 53, Slovenian Chemical Society.

Sust, "Studies on the synthesis of lubricating oils using olefins from technical C5-fractions", Energy Res., 1983, vol. 8, iss.1, abstract only.

Grudzien, "Selective solvent separation of shale oil fractions to obtain raw material for polymerization", Koks, Smola, Gaz, 1971, pp. 336-339, vol. 16, iss. 12, abstract only.

Ouyang et al., "Production technique of synthetic hydrocarbon lube oil with coking top cycle oil", Runhuayou, 2001, pp. 17-20, vol. 15, iss. 5, abstract only.

Kuliev et al., "Production of lubricating oils by alkylation of an aromatic raw material", Sbornik Trudov—Akademiya Nauk Azerbaidzhanskoi SSR, Institut Neftekhimicheskikh Protsessov im. Yu. G. Mamedalieva, 1973, pp. 128-128, vol. 5, abstract only.

Kuliev et al., "Manufacture of synthetic lubricating oils by alkylation of a secondary oil refining product", Chemische Technik, 1971, vol. 23, iss. 1, abstract only.

Takahashi et al., "Designed Oil Products from Cracked Bottom Oil", Bull Jap Petrol Inst, May 1971, pp. 103-108, vol. 13, iss. 1, abstract only.

Mursalova et al., "Alkylation of Benzene with a Wide Fraction of Alpha-Olefins (30 Degrees-250 Degrees C) Obtained by Cracking N-Paraffins (Separated in the Urea Dewaxing) of a Transformer Oil", Dokl Akad Nauk Azerb SSR, 1969, pp. 20-23, vol. 25, iss. 7, abstract only.

Kuliev, "Alkyl derivatives of petroleum hydrocarbons as lubricating oil basestocks", Khimiya i Tekhnologiya Topliv i Masel, 1997, pp. 34-35, vol. 6, abstract only.

Graves, "STRATCO Effluent Refrigerated H2SO4 Alkylation Process", Chapter 1.2 in Handbook of Petroleum Refining Processes, 3rd Ed., 2004. McGraw-Hill.

Roeseler, "UOP Alkylene Process for Motor Fuel", Chapter 1.3 in Handbook of Petroleum Refining Processes, 3rd Ed., 2004. McGraw-Hill.

Detrick et al., "UOP HF Alkylation Technology", Chapter 1.2 in Hand book of Petroleum Refining Processes, 3rd Ed., 2004 McGraw-Hill.

* cited by examiner

PROCESS TO PRODUCE PARAFFINIC HYDROCARBON FLUIDS FROM LIGHT PARAFFINS

CROSS-REFERENCE TO RELATED APPLICATIONS

This application is a continuation-in-part of copending U.S. Ser. No. 14/956,477, filed Dec. 2, 2015, now allowed, which claims the benefit of provisional U.S. Ser. No. 62/092,485, filed on Dec. 16, 2014, each of which is incorporated by reference herein in its entirety.

BACKGROUND

The present disclosure relates to a process to upgrade light paraffins, preferably C2-C5, to paraffinic hydrocarbon fluids. The process is particularly applicable to the upgrading of iso-paraffins, which are abundantly found in Natural Gas Liquids (NGL) and tight oils (produced from shale or sandstone), as well as fractions from various refining and/or chemical streams.

With the increasing production of shale gas and tight oils, the supply of light paraffins (e.g., C2-C8, especially C2-C5 paraffins) is increasing at an unprecedented rate in the North America region; a large fraction (up to 30%) of NGL, for example, is C4/C5 paraffins. At the same time, demand for C4/C5 molecules is decreasing due to a number of factors: (1) steam crackers switching feed from light naphtha to ethane; (2) shrinkage of the gasoline pool in the North American market; and (3) a potential mandate for gasoline Reid Vapor Pressure (RVP) reduction. Although diluent use of C5s for heavy crude is predicted to grow somewhat, the supply of C4s/C5s is quickly outpacing demand and the imbalance will become worse with time.

Profitable dispositions for ethane (e.g., cracking to make ethylene and propane (e.g., dehydrogenation to make propylene) exist, Upgrading C4/C5 paraffins to higher value and large volume products, while desirable, remains challenging. Conversion of C4/C5 paraffins to heavier hydrocarbon products such as gasoline, kerojet, diesel fuels, and lubricant basestocks would provide a large volume and higher value outlet to help alleviate the excess of light ends in the North American market, But there is no current commercial process directly converting light paraffins to heavier hydrocarbons such as these. Conventional upgrading practices first convert light paraffins to olefins via cracking or dehydrogenation, followed by olefin chemistries such as oligomerization or polymerization, alkylation, etc., to build higher molecular weight molecules. A number of technologies are known to convert light paraffins to aromatics such as BTX (benzene, toluene, and xylenes), including the Cyclar™ process developed by UOP and the M2-Forming process developed by Mobil Oil Corporation.

Hydrocarbon fluids (also known as hydrocarbon solvents), such as ExxonMobil's Isopar™, are high-purity synthetic iso-paraffins. Hydrocarbon fluids are widely used in paints, personal care products, industrial cleaning, machining and metal works, printer ink toners, polishing and waxing, crop protection, as well as in air fresheners. The products need to be odorless, stable, having narrow boiling ranges (for optimal combination of flash point and drying time), low aromatic content (to minimize risks from exposure), low freeze point, and compatible with most packaging materials.

Currently, paraffinic hydrocarbon fluids are experiencing increased demand. Paraffinic hydrocarbon fluids are traditionally produced via two main routes, both requiring iso-butene: (1) alkylation of iso-butene with iso-butane over an acid catalyst; and (2) oligomerization of C4 olefins such as iso-butene, followed by hydrogenation to saturate the double bond. As iso-butene is typically in limited supply, there still remains a need for a process for producing paraffinic hydrocarbon fluids using readily available feedstocks, such as light paraffins.

SUMMARY

We have now found a novel process for producing high quality hydrocarbon fluids from abundant light paraffins. In a first embodiment of the present disclosure, the process involves: (1) oxidation of iso-paraffins to alkyl hydroperoxides and alcohols; (2) conversion of the alkyl hydroperoxides and alcohols to dialkyl peroxides; and (3) radical-initiated coupling of normal-paraffins, iso-paraffins, or mixtures thereof using the dialkyl peroxides as radical initiators, thereby thrilling heavier hydrocarbon products. Fractionation of the heavy hydrocarbon products can then be used to isolate fractions for use as hydrocarbon fluids.

In another embodiment of the present disclosure, the process involves (1) oxidizing iso-butane to t-butyl hydroperoxide and t-butyl alcohol; (2) converting the t-butyl hydroperoxide and t-butyl alcohol to di-t-butyl peroxide; and (3) radical-initiated coupling of n-butane, iso-butane, or mixtures thereof using the di-t-butyl peroxide as a radical initiator to create higher paraffinic hydrocarbon products. The products are then fractionated to isolate C8 and C12 fractions for use as paraffinic hydrocarbon fluids.

DETAILED DESCRIPTION

All numerical values within the detailed description and the claims herein are modified by "about" or "approximately" the indicated value, and take into account experimental error and variations that would be expected by a person having ordinary skill in the art. The present disclosure relates to a process for making paraffinic hydrocarbon fluids from light paraffins, without requiring olefin feedstock. The process of the present disclosure involves three primary steps: (1) oxidizing one or more iso-paraffins to alkyl hydroperoxides and alcohols using air or oxygen; (2) converting the alkyl hydroperoxides and alcohols to dialkyl peroxides; and (3) radical-initiated coupling of normal-paraffins, iso-paraffins, or mixtures thereof using the dialkyl peroxide as a radical initiator to create higher paraffinic hydrocarbon products. The products are then fractionated to isolate the desired fractions for use as paraffinic hydrocarbon fluids.

In a preferred embodiment of the present disclosure, the iso-paraffin feedstock is iso-butane. The process proceeds as described generally above: (1) oxidizing the iso-butane to t-butyl hydroperoxide and t-butyl alcohol using air or oxygen; (2) converting the t-butyl hydroperoxide and t-butyl alcohol to di-t-butyl peroxide; and (3) radical-initiated coupling of iso-butane using the di-t-butyl peroxide as a radical initiator to create higher paraffinic hydrocarbon products. The products are then fractionated to isolate the C8 and C12 fractions for use as paraffinic hydrocarbon fluids.

In a further illustrative embodiment, the chemistry of Steps 1-3 with respect to iso-butane feed is shown below in corresponding Equations 1-3:

Equation 1:

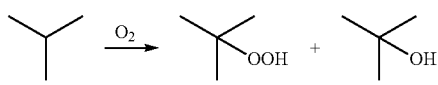

Equation 2:

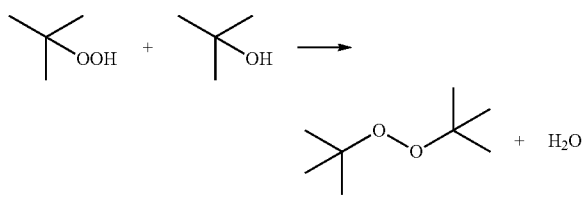

Equation 3:

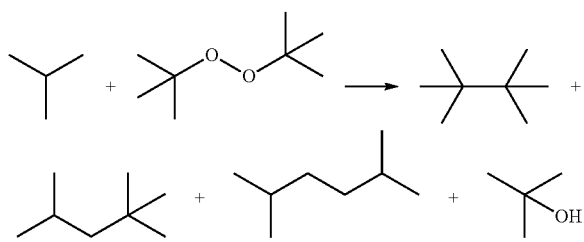

The net reaction of Equations 1-3 is oxygen (air) and iso-butane yielding heavier (C8) hydrocarbons comprising hydrocarbon fluids, as well as water and t-butyl alcohol. By controlling the reaction severity for radical coupling (Equation 3), higher molecular weight materials can also be obtained. Depending on the nature of the iso-paraffin used, the resulting alcohol can be used as high octane blend stock for gasoline, e.g., t-butyl alcohol from iso-butane, or 2-methyl-2-butanol from iso-pentane. Alternatively, the alcohols can be converted via dehydration to olefins as chemical products e.g., iso-butylene), or oligomerized or alkylated to gasoline and/or diesel range fuels, or etherified with an alcohol such as methanol or ethanol making ether as a gasoline blend (e.g., MTBE or ETBE from iso-butane).

Steps 1 and 2 have been previously described with respect to mixed paraffinic feedstocks in applicant's co-pending application, U.S. Publ. App, No. 2016/0168048, incorporated by reference herein in its entirety. U.S. Publ. App. No. 2016/0168048 describes a process to convert light paraffins to heavier hydrocarbons generally, for example, distillates and lubricant base stocks, using coupling chemistry analogous to Steps 1-3 described above. Whereas U.S. Publ. App. No. 2016/0168048 is directed to mixed paraffinic feed to create distillates and lubricant base stocks, the present disclosure utilizes analogous coupling chemistry to create a tailored paraffinic hydrocarbon fluid utilizing iso-paraffinic feedstock. U.S. Publ. App, No. 2016/0168048 further discloses upgrading raw refinery feeds, such as natural gas liquids, liquid petroleum gas, and refinery light gas such as light virgin naphtha (LVN) or light catalytic naphtha (LCN), using coupling chemistry.

Iso-butane oxidation in Step 1 is well-established commercially for making t-butyl hydroperoxide (TBHP) for propylene oxide manufacture, with variants of the process also described, for example, in U.S. Pat. No. 2,845,461; U.S. Pat. No. 3,478,108; U.S. Pat. No. 4,408,081 and U.S. Pat. No. 5,149,885. EP 0567336 and U.S. Pat. No. 5,162,593 disclose co-production of TBHP and t-butyl alcohol (TBA). As TBA is another reactant used in Step 2 of the present disclosure, the present inventive process scheme utilizes Step 1 as a practical source of these two reactants. Air (~21% oxygen), a mixture of nitrogen and oxygen containing 2-20 vol % oxygen, or pure oxygen, can be used for the oxidation, as long as the oxygen-to-hydrocarbon vapor ratio is kept outside the explosive regime. Preferably air is used as the source of oxygen. Typical oxidation conditions for Step 1 of the present disclosure are: 110-150° C. (preferably 130 to 140° C., at a pressure of about 300-800 psig (preferably about 450-550 psig), with a residence time of 2-24 hours (preferably 6-8 h), to give a targeted conversion of 15%-70% (preferably 30-50%). Selectivity to TBHP of 50-80% and to TBA of 20-50% is typical. When a mixture of nitrogen and oxygen is used, entrained iso-butane in the exhaust gas is stripped with an appropriate solvent such as TBA and may be recycled to the oxidation reactor.

In Step 2, the conversion of the TBHP and TBA to di-t-butyl peroxide (DTBP) is performed using an acid catalyst. For example, U.S. Pat. No. 5,288,919 describes the use of an inorganic heteropoly and/or isopoly acid catalyst such as for the reaction of TBA with TBHP). The conjoint production of DTBP and TBA from TBHP is also described in U.S. Pat. No. 5,345,009. A preferred configuration for the present disclosure uses reactive distillation where product water is continuously removed as overhead by-product. The typical reaction temperature is in the range of 50-200° C., preferably 60-150° C., more preferably 80-120° C. The TBHP to TBA mole ratio is in the range of 0.5-2, preferably 0.8-1.5, more preferably 0.9-1.1. The reaction can be performed with or without a solvent. Suitable solvents comprise hydrocarbons having a carbon number greater than 3, such as paraffins, naphthenes, or aromatics. Conveniently, the unreacted iso-butane from Step 1 can be used as the solvent for Step 2. Pressure for the reaction is held at appropriate ranges to ensure the reaction occurs substantially in the liquid phase, for example, 0-300 psig, preferably 5-100 psig, more preferably 15-50 psig. An acid catalyst such as Amberlyst™ resin, Nafion™ resin, aluminosilicates, acidic clay, zeolites (natural or synthetic), silicoaluminophosphates (SAPO), heteropolyacids, acidic oxides such as tungsten oxide on zirconia, molybdenum oxide on zirconia, sulfuated zirconia, liquid acids such sulfuric acid, or acidic ionic liquids may be used in Step 2/Equation 2 to promote the conversion of TBHP and TBA into DTBP.

In Step 3/Equation 3, DTBP is introduced to a coupling reactor to initiate free radical coupling of iso-butane feed. Typical reaction conditions for Step 3 of the present disclosure are: 100-170° C. (preferably about 145-155° C.), with pressure maintained to ensure that iso-butane stays in the liquid or supercritical phase, typically 700-1500 psig (preferably about 850-950 psig). Residence time is normally in the range of 2-24 hours (preferably 4-16 hours). The molar ratio of DTBP to iso-butane to be coupled is in the range of about 0.01-100, preferably in the range of about 0.05-10, and more preferably in the range of 0.1-2. Complete conversion of DTBP is normally achieved in this step.

Following Step 3, the mixed products are then fractionated to remove unreacted iso-butane and TBA, byproduct acetone, and to separate various grades of paraffinic hydrocarbon fluids. For example, a C8 fraction (particularly 2,2,4-trimethylpentane) can be used as light paraffinic fluids, and the C12 fraction can be used as heavier paraffinic fluids. The hydrocarbon fluids of the present disclosure may also be hydro-finished to remove trace oxygenates or unsaturation, by processes well known in the art.

EXAMPLE

In order to provide a better understanding of the foregoing disclosure, the following non-limiting example is offered.

Although the example may be directed to specific embodiments, they are not to be viewed as limiting the disclosure in any specific respect.

This example illustrates the general procedure for coupling iso-butane using DTBP. In a 300 cc autoclave the following were loaded: 100 cc (59.5 g) of iso-butane (Airgas, instrument grade) and 56 g of DTBP (trade name Luperox DI from Aldrich Chemicals, 98%). The autoclave was sealed, connected to a gas manifold, and pressurized with 600 psig nitrogen. The reactor content heated under stirring (500 rpm) at a rate of 2° C./min to 150° C. and held for 4 hours. The heat was turned off and the autoclave allowed to cool down to room temperature. A sample was taken and analyzed by GC, showing complete conversion of DTBP. The autoclave was opened and the reactor content collected at the end of the run, recovering 88% of the materials loaded. The products were analyzed by GC. The run was repeated using different loadings of DTBP. The results are shown below in Table 1.

TABLE 1

| | Reaction temperature (° C.) | | | | | | | |
|---|---|---|---|---|---|---|---|---|
| | 150 | 150 | 150 | 150 | 135 | 135 | 135 | 135 |
| Time (h) | 4 | 4 | 4 | 4 | 21 | 21 | 21 | 21 |
| Iso-butane loading, g | 59.4 | 59.4 | 59.4 | 59.4 | 59.4 | 59.4 | 59.4 | 59.4 |
| DTBP loading, g | 56.0 | 40.0 | 24.0 | 16.0 | 56.0 | 40.0 | 24.0 | 16.0 |
| HC wt. sel. (%) | | | | | | | | |
| 2,2,4-trimethylpentane | 13.48 | 14.26 | 13.05 | 15.48 | 14.61 | 16.50 | 16.38 | 16.08 |
| 2,4,4-trimethyl-1-pentene | 0.22 | 0.46 | 1.64 | 3.42 | 0.17 | 0.20 | 0.82 | 1.52 |
| 2,2,3,3-tetramethylbutane | 19.35 | 18.88 | 18.67 | 18.67 | 17.55 | 19.63 | 17.44 | 16.77 |
| 2,4,4-trimethyl-2-pentene | 0.29 | 0.35 | 0.48 | 0.55 | 0.16 | | | |
| 2,2,3-trimethylpentane | 1.32 | | | | 0.28 | 0.32 | 0.42 | 0.47 |
| 2,5-dimethylhexane | 1.18 | 1.49 | 1.55 | 1.48 | 1.42 | 1.29 | 1.29 | 1.14 |
| 4,4-dimethyl-2-pentanone | 0.94 | 11.06 | 9.14 | 9.08 | 0.46 | 4.84 | 7.48 | 6.29 |
| 2,2,4,4-tetramethylpentane | 0.76 | 0.56 | 0.30 | 0.21 | 0.40 | 0.46 | 0.22 | 0.15 |
| 2,2,4-trimethylhexane | 1.44 | 0.65 | 0.51 | 0.42 | 1.00 | 0.43 | 0.25 | 0.20 |
| 2,4,4-trimethylhexane | 0.40 | 1.41 | 1.32 | 1.16 | 0.27 | 1.12 | 0.84 | 0.72 |
| 2,2,3,3-tetramethylpentane | 1.55 | 0.58 | 0.93 | 1.12 | 0.74 | 0.17 | 0.44 | 0.56 |
| C9 | 12.83 | 10.69 | 8.38 | 6.81 | 8.52 | 7.99 | 8.82 | 4.57 |
| C12 | 5.51 | 8.33 | 14.21 | 16.40 | 6.98 | 7.83 | 15.25 | 20.57 |
| C16+ | 33.29 | 36.49 | 35.20 | 30.94 | 42.09 | 37.81 | 34.43 | 34.57 |
| Oxygenates wt. sel. (%) | | | | | | | | |
| Acetone | 30.6 | 28.7 | 22.6 | 22.0 | 21.0 | 21.7 | 15.8 | 13.2 |
| t-Butanol | 69.4 | 71.3 | 77.4 | 78.0 | 79.0 | 78.3 | 84.2 | 86.8 |

As demonstrated in Table 1, light (C8-C9) and heavy (C12) paraffinic fluids can be produced from certain teachings of the present disclosure. One of skill in the art will appreciate that key variables, including reaction temperature, molar ratio of DTBP to iso-butane, and residence time, can be adjusted to tailor the heavier hydrocarbon product for specific paraffinic hydrocarbon fluid applications.

ADDITIONAL EMBODIMENTS

Embodiment 1

A process for the conversion of paraffins to paraffinic hydrocarbon fluids, comprising oxidizing iso-paraffins from a first paraffinic feed with air or oxygen to form alkyl hydroperoxides and alcohols, catalytically converting the alkyl hydroperoxides and alcohols to dialkyl peroxides, and coupling a second paraffinic feed using the dialkyl peroxides as radical initiators to create hydrocarbon fluids.

Embodiment 2

A process according to any of the previous embodiments, wherein the first paraffinic feed comprises normal paraffins, iso-paraffins, or mixtures thereof.

Embodiment 3

A process according to any of the previous embodiments, further comprising isomerizing at least a fraction of the normal paraffins to iso-paraffins prior to the oxidizing step.

Embodiment 4

A process according to any of the previous embodiments, wherein the second paraffinic feed comprises normal paraffins, iso-paraffins, or mixtures thereof.

Embodiment 5

A process according to any of the previous embodiments, further comprising fractionating the paraffinic hydrocarbon fluids to isolate a desired fraction.

Embodiment 6

A process according to any of the previous embodiments, wherein the first paraffinic feed and the second paraffinic feed are independently selected from normal paraffins with 4 or 5 carbon numbers, iso-paraffins with 4 or 5 carbon numbers, and mixtures thereof.

Embodiment 7

A process according to any of the previous embodiments, wherein the iso-paraffins of the oxidizing step are selected from iso-butane, iso-pentane, and mixtures thereof.

Embodiment 8

A process according to any of the previous embodiments, wherein the iso-paraffins of the oxidizing step comprise 60 to 99 wt % iso-butane.

Embodiment 9

A process according to any of the previous embodiments, wherein the second paraffinic feed comprises less than 50 wt % olefins.

Embodiment 10

A process according to any of the previous embodiments, wherein the second paraffinic feed comprises less than 10 wt % olefins.

Embodiment 11

A process according to any of the previous embodiments, wherein the second paraffinic feed comprises less than 5 wt % olefins.

Embodiment 12

A process according to any of the previous embodiments, wherein the first paraffinic feed comprises butanes.

Embodiment 13

A process according to any of the previous embodiments, wherein the first paraffinic feed comprises 5 to 90 wt % iso-butane.

Embodiment 14

A process according to any of the previous embodiments, further comprising substantially isomerizing n-butane in the first paraffinic feed to iso-butane.

Embodiment 15

A process according to any of the previous embodiments, wherein the first paraffinic feed comprises pentanes.

Embodiment 16

A process according to any of the previous embodiments, wherein the first paraffinic feed comprises 5 to 90 wt % iso-pentane.

Embodiment 17

A process according to any of the previous embodiments, further comprising substantially isomerizing n-pentane in the first paraffinic feed to iso-pentane.

Embodiment 18

A process according to any of the previous embodiments, wherein iso-paraffins are separated from normal paraffins in the first paraffinic feed, and the separated normal paraffins are used as the second paraffinic feed.

Embodiment 19

A process according to any of the previous embodiments, wherein iso-paraffins are separated from normal paraffins in the first paraffinic feed, and the separated iso-paraffins are used as the second paraffinic feed.

Embodiment 20

A process according to any of the previous embodiments, wherein the hydrocarbon fluids are hydro-finished to remove trace oxygenates or unsaturation.

Embodiment 21

A process according to any of the previous embodiments, wherein the conversion of alkyl hydroperoxides to dialkyl peroxides in the catalytic conversion step is carried out by reactive distillation.

Embodiment 22

A process according to any of the previous embodiments, wherein the coupling step is carried out in a reactor selected from batch, CSTR, and plug-flow.

Embodiment 23

A process for the conversion of iso-butane and normal butane to paraffinic hydrocarbon fluids, comprising oxidizing iso-butane to form t-butyl hydroperoxide and t-butyl alcohol, catalytically converting the t-butyl hydroperoxide and the t-butyl alcohol to di-t-butyl peroxide, and coupling a paraffinic feed using the di-t-butyl peroxide as a radical initiator to create hydrocarbon fluids.

Embodiment 24

A process according to embodiment 23, further comprising fractionating the hydrocarbon fluids to isolate C8 and C12 fractions.

Embodiment 25

A process according to any of the previous embodiments, wherein the paraffinic feed comprises normal butane, iso-butane, or mixtures thereof.

Embodiment 26

A process according to any of the previous embodiments, wherein the paraffinic feed comprises less than 10 wt % olefins.

Embodiment 27

A process according to any of the previous embodiments, wherein the paraffinic feed comprises less than 5 wt % olefins.

Embodiment 28

A process according to any of the previous embodiments, wherein the hydrocarbon fluids are hydro-finished to remove trace oxygenates or unsaturation.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings therein. It is therefore evident that the particular embodiments disclosed above may be altered or modified and all such variations are considered within the scope and sprit of the present disclosure. Unless otherwise indicated, all numbers expressing quantities of ingredients, properties, reaction conditions, and so forth, used in the specification and claims are to be understood as approximations based on the desired properties sought to be obtained by the present disclosure. Whenever a numerical range with a lower limit and an upper limit is disclosed, a number falling within the range is specifically disclosed. Moreover, the indefinite articles "a" or "an", as used in the claims, are defined herein to mean one or more than one of the element that it introduces.

The invention claimed is:

1. A process for the conversion of paraffins to paraffinic hydrocarbon fluids, comprising:
   a) oxidizing iso-paraffins from a first paraffinic feed with air or oxygen to form alkylhydroperoxides and alcohols;
   b) catalytically reacting the alkyl hydroperoxides with said alcohols from step (a) to form dialkyl peroxides; and
   c) providing a second paraffinic feed comprising paraffins using the dialkyl peroxides from step (b) as radical initiators to couple paraffins with paraffins to create paraffinic hydrocarbon fluids comprising other branched and heavier paraffins and a second alcohol;
   wherein the first paraffinic feed and the second paraffinic feed are independently selected from normal paraffins with 4 or 5 carbon numbers, iso-paraffins with 4 or 5 carbon numbers, and mixtures thereof.

2. The process of claim 1, further comprising isomerizing at least a fraction of the normal paraffins to iso-paraffins prior to step (a).

3. The process of claim 1, further comprising fractionating the paraffinic hydrocarbon fluids to isolate a desired fraction.

4. The process of claim 1, wherein the iso-paraffins of step (a) are selected from iso-butane, iso-pentane, and mixtures thereof.

5. The process of claim 1, wherein the iso-paraffins of step (a) comprise 60 to 99 wt % iso-butane.

6. The process of claim 1, wherein the second paraffinic feed comprises less than 50 wt % olefins.

7. The process of claim 1, wherein the second paraffinic feed comprises less than 10 wt % olefins.

8. The process of claim 1, wherein the second paraffinic feed comprises less than 5 wt % olefins.

9. The process of claim 1, wherein the first paraffinic feed comprises butanes.

10. The process of claim 9, wherein the first paraffinic feed comprises 5 to 90 wt % iso-butane.

11. The process of claim 9, further comprising substantially isomerizing n-butane in the first paraffinic feed to iso-butane.

12. The process of claim 1, wherein the first paraffinic feed comprises pentanes.

13. The process of claim 12, wherein the first paraffinic feed comprises 5 to 90 wt % iso-pentane.

14. The process of claim 12 further comprising substantially isomerizing n-pentane in the first paraffinic feed to iso-pentane.

15. The process of claim 1, wherein iso-paraffins are separated from normal paraffins in the first paraffinic feed, and the separated normal paraffins are used as the second paraffinic feed.

16. The process of claim 1, wherein iso-paraffins are separated from normal paraffins in the first paraffinic feed, and the separated iso-paraffins are used as the second paraffinic feed.

17. The process of claim 1, wherein the paraffinic hydrocarbon fluids are hydro-finished to remove trace oxygenates or unsaturation.

18. The process of claim 1, the reaction in step (b) is carried out by reactive distillation.

19. The process of claim 1, wherein the coupling reaction of step (c) is carried out in a reactor selected from batch, CSTR, and plug-flow.

20. A process for the conversion of iso-butane and normal butane to paraffinic hydrocarbon fluids, comprising:
   a) oxidizing iso-butane to form t-butyl hydroperoxide and t-butyl alcohol;
   b) catalytically reacting the t-butyl hydroperoxide with the t-butyl alcohol from step (a) to di-t-butyl peroxide; and
   c) providing a paraffinic feed comprising paraffins using the di-t-butyl peroxide from step (b) as a radical initiator to couple paraffins with paraffins to create hydrocarbon fluids comprising other branched and heavier paraffins and a second alcohol, wherein the paraffinic feed comprises normal butane, iso-butane, or mixtures thereof.

21. The process of claim 20, further comprising: (d) fractionating the hydrocarbon fluids to isolate C8 and C12 fractions.

22. The method of claim 20, wherein the paraffinic feed comprises less than 10 wt % olefins.

23. The method of claim 20, wherein the paraffinic feed comprises less than 5 wt % olefins.

24. The method of claim 20, wherein the hydrocarbon fluids are hydro-finished to remove trace oxygenates or unsaturation.

* * * * *